US008181958B2

United States Patent
Yamamoto et al.

(10) Patent No.: US 8,181,958 B2
(45) Date of Patent: May 22, 2012

(54) STIFFNESS DETECTOR, STIFFNESS DETECTION METHOD, AND PAPER SHEET PROCESSOR INCLUDING STIFFNESS DETECTOR

(75) Inventors: Takahiro Yamamoto, Fuchu (JP); Kazuhiro Itsumi, Tokyo (JP); Seiji Ikari, Yokohama (JP); Takanobu Nishimura, Chigasaki (JP); Yoshihiko Naruoka, Yokohama (JP); Toru Todoriki, Kawasaki (JP); Junji Miura, Naka-gun (JP); Takahisa Nakano, Kawasaki (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 194 days.

(21) Appl. No.: 12/717,357

(22) Filed: Mar. 4, 2010

(65) Prior Publication Data

US 2011/0001285 A1 Jan. 6, 2011

(30) Foreign Application Priority Data

Jul. 2, 2009 (JP) .................................. 2009-157956

(51) Int. Cl.
*B65H 7/02* (2006.01)
(52) U.S. Cl. .............................. 271/265.04; 271/265.01
(58) Field of Classification Search ............. 271/265.01, 271/265.02, 265.04, 262
See application file for complete search history.

(56) References Cited

U.S. PATENT DOCUMENTS

| 6,441,904 B1 | 8/2002 | Shakespare |
| 6,520,498 B2 * | 2/2003 | Phinney .................. 271/263 |
| 7,025,348 B2 * | 4/2006 | Phinney et al. ............ 271/262 |

FOREIGN PATENT DOCUMENTS

| DE | 102007000263 | 11/2008 |
| FR | 2661749 A1 | 11/1991 |
| JP | 05-80605 | 11/1993 |
| JP | 2008-164394 | 7/2008 |
| SU | 563621 A1 | 6/1977 |

OTHER PUBLICATIONS

Takahiro Yamamoto, U.S. Appl. No. 12/717,383.
European Search Report dated Sep. 13, 2010.

* cited by examiner

*Primary Examiner* — Michael McCullough
(74) *Attorney, Agent, or Firm* — Pillsbury Winthrop Shaw Pittman, LLP

(57) ABSTRACT

A stiffness detector includes a bending portion configured to bend a paper sheet to be carried. The stiffness detector transmits acoustic waves to an incidence point on an inner surface of the paper sheet which is bent by the bending portion and is carried, thereby exciting Lamb waves. The stiffness detector receives leaky waves of the Lamb waves emitted from a detection point on the inner surface of the paper sheet. The stiffness detector specifies a maximum crest value based on the received signals, and judges whether the paper sheet is an unimpaired sheet based on the specified maximum crest value.

10 Claims, 10 Drawing Sheets

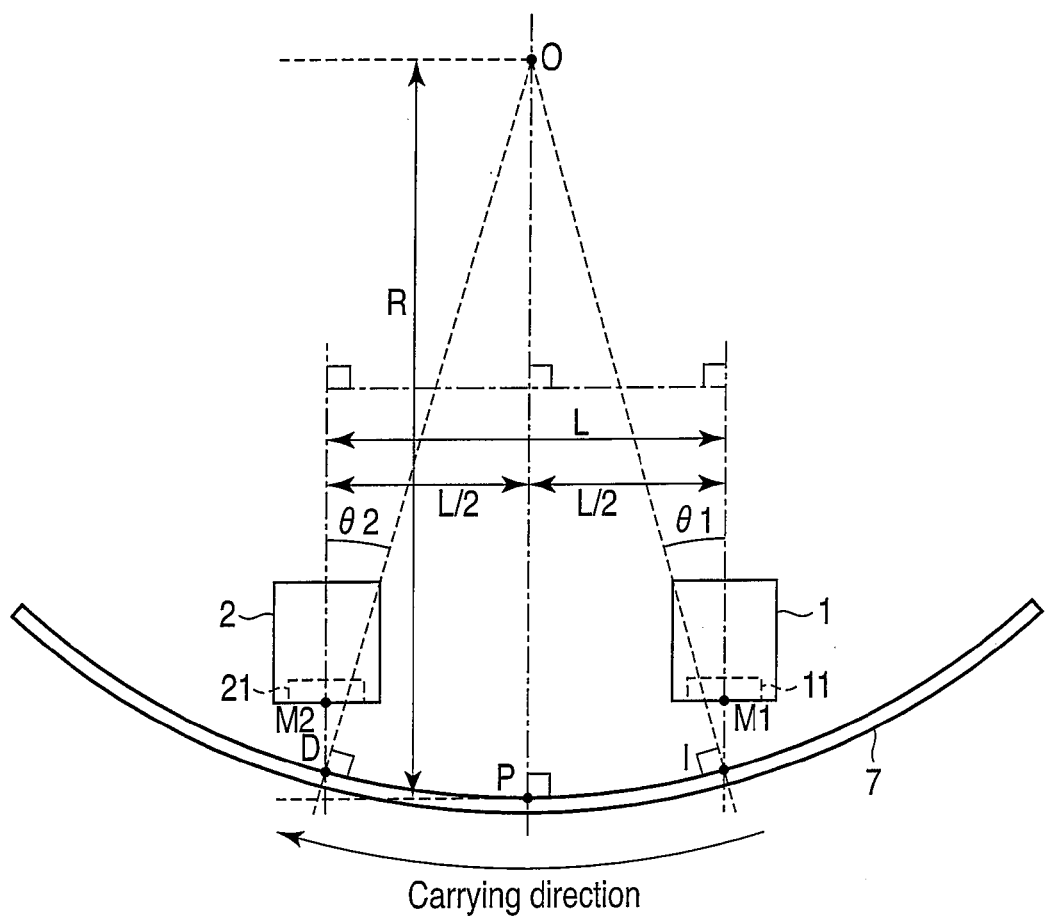
F I G. 3
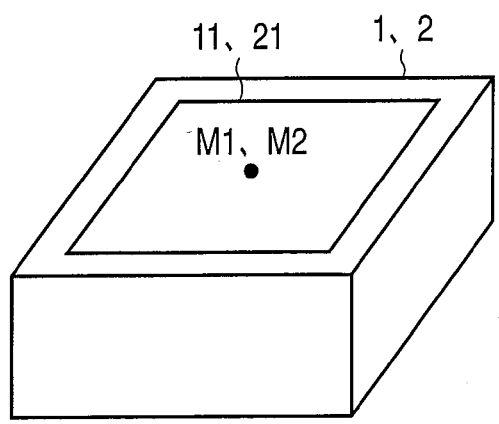
F I G. 4

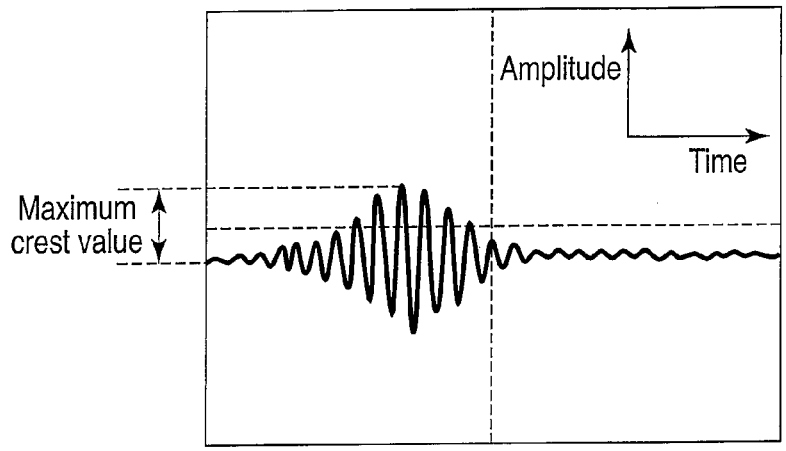
F I G. 7
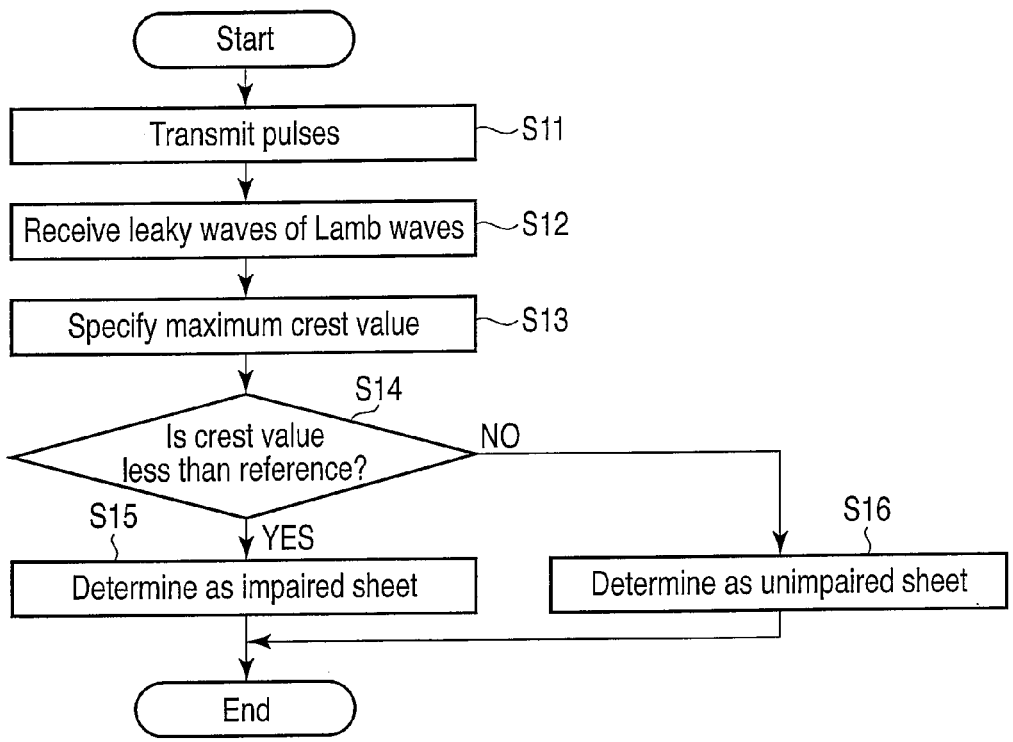
F I G. 8

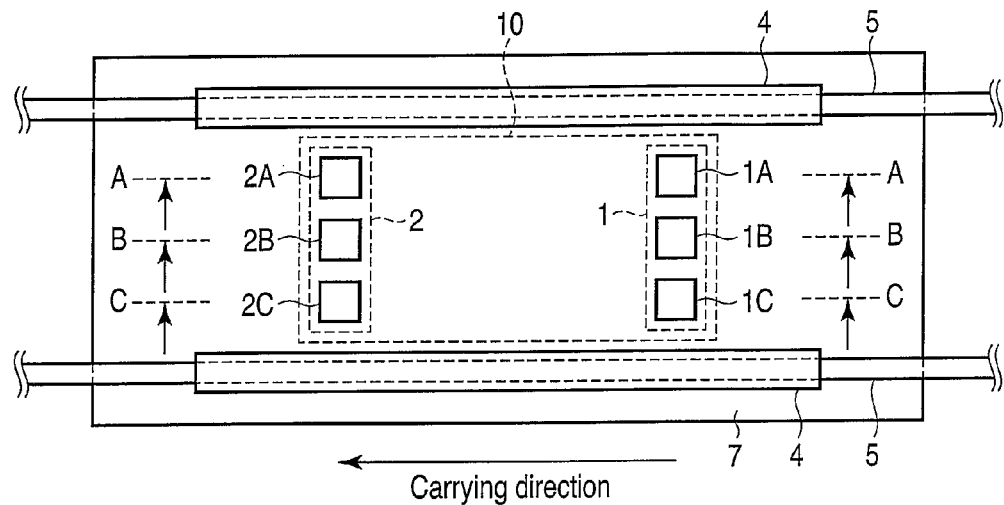
F I G. 11
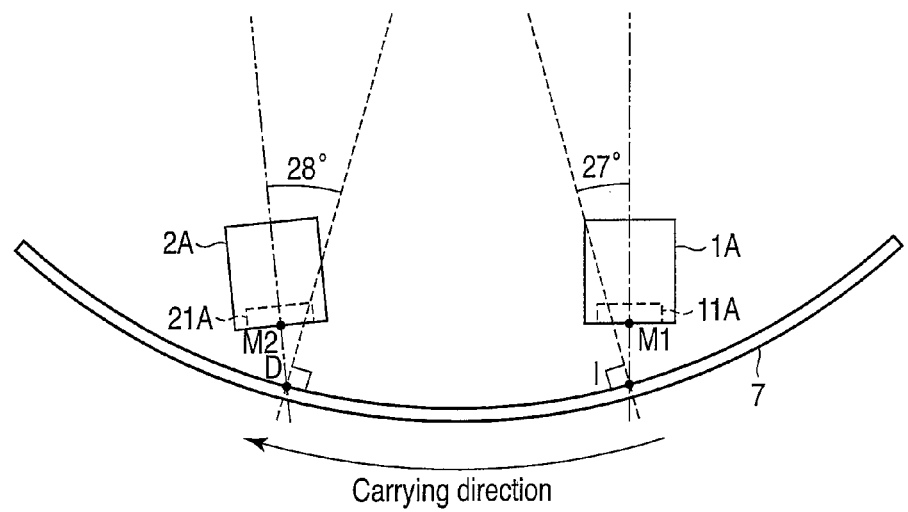
F I G. 12

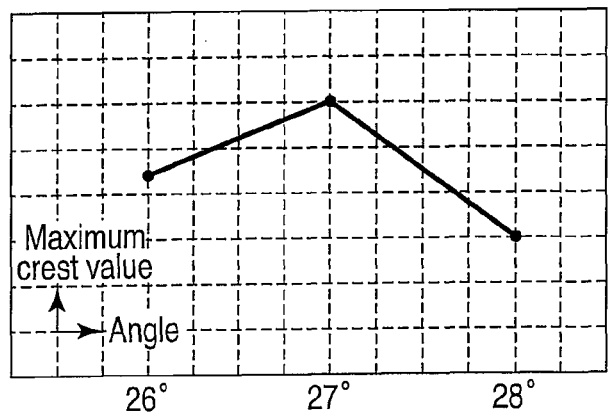
F I G. 15
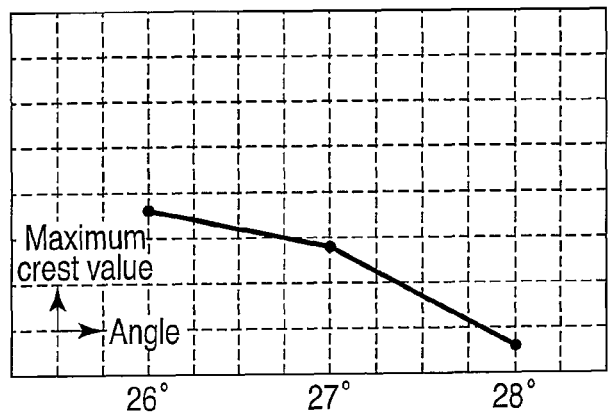
F I G. 16
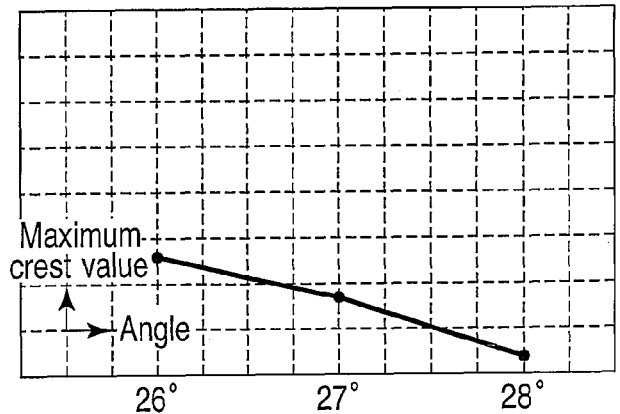
F I G. 17

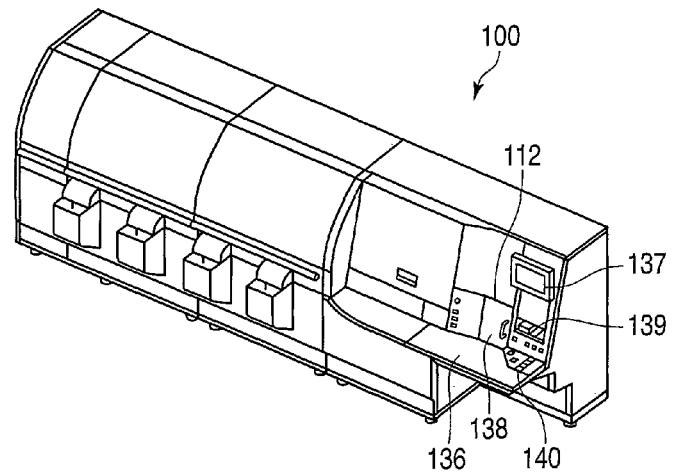
F I G. 18
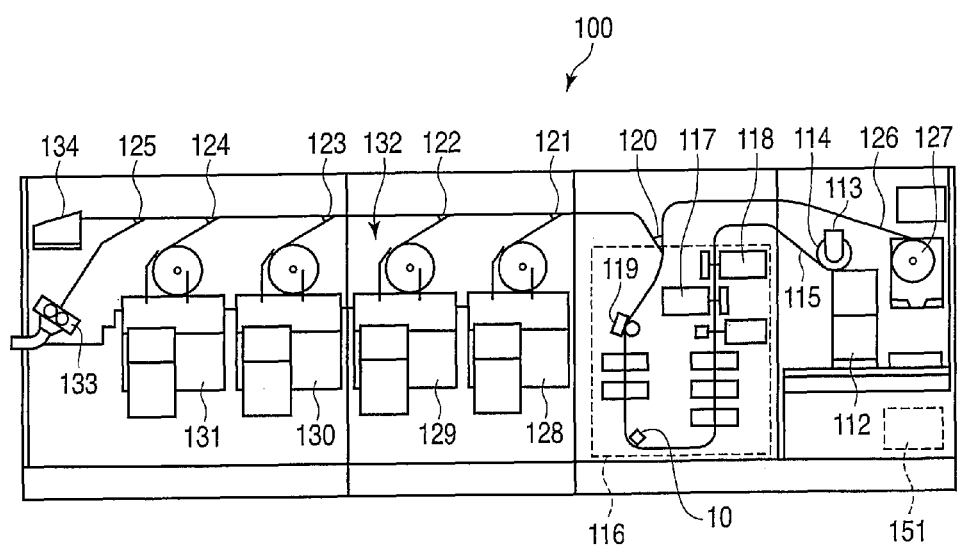
F I G. 19

STIFFNESS DETECTOR, STIFFNESS DETECTION METHOD, AND PAPER SHEET PROCESSOR INCLUDING STIFFNESS DETECTOR

CROSS-REFERENCE TO RELATED APPLICATIONS

This application is based upon and claims the benefit of priority from prior Japanese Patent Application No. 2009-157956, filed Jul. 2, 2009, the entire contents of which are incorporated herein by reference.

BACKGROUND OF THE INVENTION

1. Field of the Invention

The present invention relates to a stiffness detector that detects stiffness of a paper sheet, a stiffness detection method, and a paper sheet processor including the stiffness detector.

2. Description of the Related Art

A paper sheet processor that counts and discriminates various kinds of paper sheets has been put to practical use. The paper sheet processor takes in paper sheets put in an injection module one by one and carries them to an examination device for paper sheets. The examination device executes various kinds of processing with respect to paper sheets to judge states of the paper sheets. If the paper sheet is, e.g., a paper currency, the paper sheet processor executes a judgment on a type of each paper sheet, a true-false judgment, a judgment upon whether a paper sheet can be again circulated (a wear judgment), and others based on an examination result obtained by the examination device.

The paper sheet processor determines paper sheets having degraded stiffness as paper sheets that are not suitable for recirculation. Therefore, the examination device detects mechanical characteristics such as a degree of deterioration in stiffness of paper sheets.

For example, Jpn. Pat. Appln. KOKAI Publication No. 5-80605 as a Japanese patent document discloses a technology for transmitting acoustic waves to a paper sheet and measuring a weight per unit area of the paper sheet based on a level of reflected waves or transmitted waves.

Further, Jpn. Pat. Appln. KOKAI Publication No. 2008-164394 as a Japanese patent document discloses a technology for causing ultrasonic waves to enter a sample such as a metal plate, receiving leaky waves of waves propagated through the sample, and detecting a defect in the sample based on an amplitude of a received waveform.

In the apparatus having the above-described configuration, for example, when a transmitter that transmits acoustic waves and a receiver that receives acoustic waves are arranged to face each other, crosstalk that acoustic waves output from the transmitter directly enter the receiver without the intermediary of a paper sheet occurs.

The technology disclosed in Jpn. Pat. Appln. KOKAI Publication No. 5-80605 prevents the acoustic waves from entering the receiver without the intermediary of the paper sheet by providing an acoustic absorbent. However, there is a problem that the acoustic waves may possibly enter the receiver when they are diffracted.

Further, as described in Jpn. Pat. Appln. KOKAI Publication No. 5-80605, when receiving transmitted waves or reflected waves, there is a limit in installing positions of the transmitter and the receiver. Therefore, there is a problem that a size of the apparatus increases.

Furthermore, the technology disclosed in Jpn. Pat. Appln. KOKAI Publication No. 2008-164394 has a problem that a factor of a defect cannot be specified when detecting the defect in a sample. That is, it has a problem that a factor of a detected defect which may be a reduction in an elastic modulus, breakage, crack, or crease cannot be determined.

BRIEF SUMMARY OF THE INVENTION

According to one embodiment of the invention, a stiffness detector, a stiffness detection method, a paper sheet processor can be provided, all of which highly accurately detect the stiffness of paper sheets in a compact configuration.

A stiffness detector, which is an embodiment of this invention, comprising: a bending portion configured to bend a paper sheet to be carried; a transmission module configured to transmit acoustic waves to an incidence point on an inner surface of the paper sheet which is bent by the bending portion and is carried, thereby exciting Lamb waves; a reception module configured to receive leaky waves of the Lamb waves emitted from a detection point on the inner surface of the paper sheet; and a first judgment module configured to specify a maximum crest value based on an output from the reception module and judge whether the paper sheet is an unimpaired sheet based on the specified maximum crest value.

A stiffness detection method, which is an embodiment of this invention, comprising: transmitting acoustic waves to an incidence point on an inner surface of a paper sheet which is bent and carried, thereby exciting Lamb waves; receiving leaky waves of the Lamb waves emitted from a detection point on the inner surface of the paper sheet; and specifying a maximum crest value based on a received signal to judge whether the paper sheet is an unimpaired sheet based on the specified maximum crest value.

A paper sheet processor, which is an embodiment of this invention, comprising: a carriage module configured to carry a paper sheet; a bending portion configured to bend the paper sheet carried by the carriage module; a transmission module configured to transmit acoustic waves to an incidence point on an inner surface of the paper sheet which is bent by the bending portion and is carried, thereby exciting Lamb waves; a reception module configured to receive leaky waves of the Lamb waves emitted from a detection point on the inner surface of the paper sheet; a judgment module configured to specify a maximum crest value based on an output from the reception module to judge whether the paper sheet is an unimpaired sheet based on the specified maximum crest value; and a classification processing module configured to classify the paper sheet based on a judgment result obtained from the judgment module.

Thus, this invention can provide a stiffness detector, a stiffness detection method, a paper sheet processor can be provided, all of which highly accurately detect the stiffness of paper sheets in a compact configuration.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWINGS

FIG. 3 is an explanatory view for explaining an example of arrangement of each module in the stiffness detector;

FIG. 4 is an explanatory view for explaining an example of a configuration of a transmission module and a reception module in the stiffness detector;

FIG. 7 is an explanatory view for explaining an example of a waveform received by the reception module;

FIG. 8 is a flowchart for explaining an operation of the stiffness detector;

FIG. 11 is an explanatory view for explaining a structural example of a stiffness detector according to another embodiment;

FIG. 12 is an explanatory view for explaining an example of arrangement of each module in the stiffness detector depicted in FIG. 11;

FIG. 15 is an explanatory view for explaining a relationship between a crest value of a waveform received by each reception module and an angle of the reception module in the stiffness detector depicted in FIG. 11;

FIG. 16 is an explanatory view for explaining a relationship between a crest value of a waveform received by each reception module and an angle of the reception module in the stiffness detector depicted in FIG. 11;

FIG. 17 is an explanatory view for explaining a relationship between a crest value of a waveform received by each reception module and an angle of the reception module in the stiffness detector depicted in FIG. 11;

FIG. 18 is an explanatory view for explaining an appearance of a paper sheet processor according to an embodiment;

FIG. 19 is an explanatory view for explaining a structural example of the paper sheet processor depicted in FIG. 18.

DETAILED DESCRIPTION OF THE INVENTION

A stiffness detector, a stiffness detection method, and a paper sheet processor including the stiffness detector according to an embodiment of the present invention will now be described hereinafter in detail with reference to the accompanying drawings.

Figure 1:
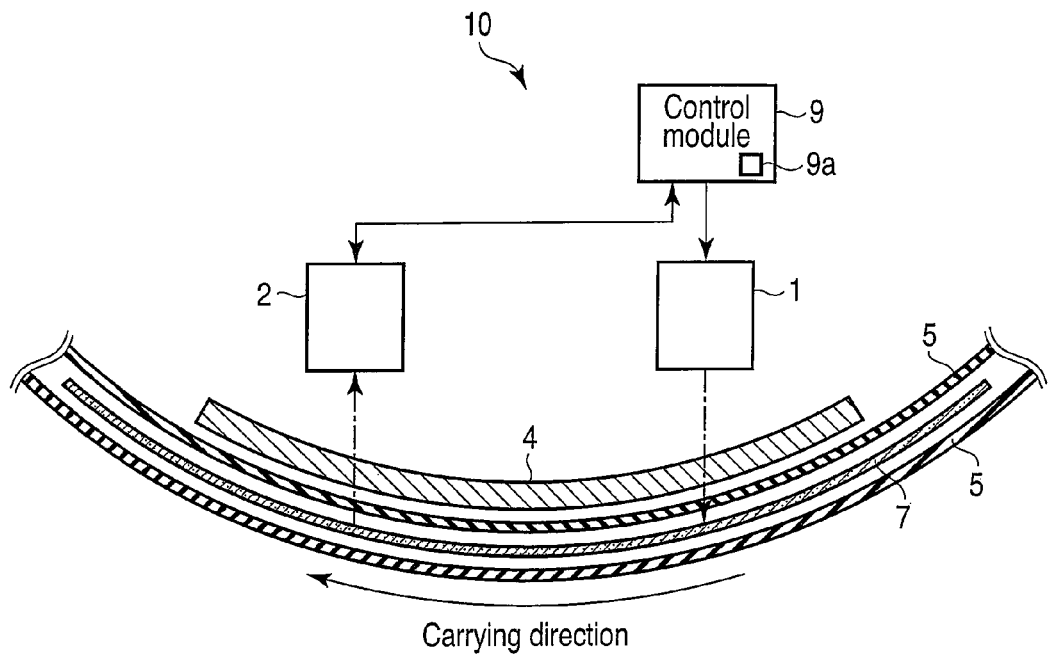
FIG. 1 is an explanatory view for explaining a structural example of a stiffness detector according to an embodiment.

FIG. 1 is an explanatory view for explaining a structural example of a stiffness detector according to an embodiment.

The stiffness detector 10 checks mechanical properties of a paper sheet 7. For example, the stiffness detector 10 detects stiffness such as an elastic modulus, tensile strength or bending strength of the paper sheet 7.

As shown in FIG. 1, the stiffness detector 10 includes a transmission module 1, a reception module 2, a guide plate 4 and a control module 9. The transmission module 1, the reception module 2 and the guide plate 4 are disposed on one surface side of the paper sheet 7 to be carried.

The transmission module 1 is a transmitter of ultrasonic waves that excite Lamb waves (plate waves) in the paper sheet 7. The transmission module 1 includes, e.g., a speaker, a piezoelectric transducer or a vibration generator using a micro electro mechanical system (MEMS). The transmission module 1 vibrates an vibration plane in accordance with an applied voltage, thereby generating acoustic waves. The transmission module 1 is disposed on an upstream side of the reception module 2.

The reception module 2 is a receiver that detects a waveform of the Lamb waves generated in the paper sheet 7. The reception module 2 has the same configuration as the transmission module 1. The reception module 2 includes, e.g., a microphone, a piezoelectric transducer, a displacement gauge (an interferometer) using interfering light that measures vibration as displacement, and others. The reception module 2 obtains a voltage in accordance with vibration of a vibration plane excited by waves leaking from the paper sheet 7.

The transmission module 2 and the reception module 2 perform processing with respect to the paper sheet 7 to be carried. When emitting acoustic waves to the paper sheet 7 in a non-contact manner, the attenuation of the acoustic waves is large. Therefore, the stiffness detector is disposed at a position close to the paper sheet 7 carried by conveying belts 5.

The conveying belts 5 function as a conveyance module. The conveying belts 5 include a pair of upper and lower belts as shown in FIG. 1. The conveying belts 5 are driven by driving pulleys or the like. The conveying belts 5 use the pair of upper and lower belts to sandwich the paper sheet 7 and convey it at a fixed speed.

The guide plate 4 is provided along the predetermined conveying belts 5. As shown in FIG. 1, the guide plate 4 is formed to bend in a direction along which it curls toward the side where the transmission module 1 and the reception module 2 are disposed, i.e., a direction vertical to the carrying direction of the paper sheet 7.

When pressing the guide plate 4 against the carrying belts 5 from the side where the transmission module 1 and the reception module 2 are disposed, the conveying belts 5 bend with the same curvature as the guide plate 4. As a result, the stiffness detector 10 can carry the paper sheet 7 in a bent state. It is to be noted that the guide plate 4 may be formed of any material as long as it can bend the conveying belts 5.

The control module 9 controls the entire stiffness detector 10. The control module 9 includes a CPU, a buffer memory, a program memory, a nonvolatile memory and others. The CPU executes various kinds of arithmetic processing. The buffer memory temporarily stores arithmetic results. The program memory and the nonvolatile memory store various kinds of programs executed by the CPU, control data and others. The control module 9 can execute various kinds of processing by using the CPU to perform a program stored in the program memory. For example, the control module 9 controls operation timings of the transmission module 1 and the reception module 2.

When detecting the paper sheet 7, the stiffness detector 10 generates ultrasonic waves from the transmission module 1. As a result, the stiffness detector 10 applies ultrasonic waves to the paper sheet 7. In the paper sheet 7, the Lamb waves are excited by the ultrasonic waves. The excited Lamb waves generate leaky waves from a surface of the paper sheet 7 while being propagated through the paper sheet 7. The stiffness detector 10 detects the leaky waves of the Lamb waves by using the reception module 2.

The Lamb wave is a wave whose vibrating direction is vertical to a medium and which is propagated in a propagating direction with the same vibration component. The Lamb wave is a wave that is propagated through a medium having substantially the same thickness as a wavelength. The Lamb wave has characteristics that it can be detected at any point in the medium through which this wave is propagated, its acoustic velocity can be calculated from a propagation time, it is affected when a medium is not uniform, or a signal intensity does not fluctuate when held, for example.

The paper sheet 7 is constituted of fibers and a binder. However, when the paper sheet 7 is fatigued, the binder becomes deficient, and a contained amount of air relatively increases. As a result, a density of the fatigued paper sheet 7 is lower than that of a non-fatigued paper sheet. When a ratio of air in the paper sheet 7 increases, properties of air become closer to properties of the paper sheet 7, thereby lowering an acoustic resistance value. That is, the Lamb waves propagated through the paper sheet 7 are apt to leak to the outside. Therefore, the Lamb waves are attenuated and an amplitude thereof is reduced before reaching a detection point of the reception module 2.

Furthermore, when emitting ultrasonic waves to the paper sheet 7 from the transmission module 1, the transmission module 1 emits acoustic waves to the paper sheet 7 at an optimum incidence angle θ for the surface of the paper sheet 7. As a result, the amplitude of the Lamb waves generated in the paper sheet 7 becomes maximum. Moreover, a leak amount of the leaky waves of the Lamb waves propagated through the paper sheet 7 varies in accordance with an angle (an output angle) at which the leaky waves exit from the paper sheet 7. The leak amount becomes maximum at the same output angle as the optimum incidence angle (a maximum leak angle).

The optimum incidence angle θ is determined based on air and characteristics of the paper sheet 7 to be examined. Assuming that a velocity of sound propagated through air is Ca and a velocity of sound propagated through the paper sheet 7 is Cs, the optimum incidence angle θ can be determined based on the following Expression 1.

$$\sin\theta = \frac{Ca}{Cs} \quad \text{(Expression 1)}$$

It is to be noted that the respective acoustic velocities Ca and Cs are determined based on the following Expression 2.

$$\text{velocities } C = \sqrt{\frac{\text{stiffness}}{\text{density}}} \quad \text{(Expression 2)}$$

As described above, in case of the fatigued paper sheet 7, a velocity of the waves propagated through the paper sheet 7 is reduced. As a result, a value of sin θ varies, and the optimum incidence angle θ changes. When the properties of the paper sheet 7 have come closer to those of air, the density is reduced, and hence the optimum incidence angle θ is decreased. Therefore, in this embodiment, the maximum leak angle of the non-fatigued paper sheet 7 is determined as a reference angle, and the reception module 2 is disposed at the reference angle with respect to the paper sheet 7.

It is to be noted that the description will be given on the assumption that the reference angle of the non-fatigued paper sheet 7 is 27 degrees in this embodiment.

As described above, the control module 9 in the stiffness detector 10 according to this embodiment judges whether the paper sheet 7 is an unimpaired sheet or an impaired sheet based on an output from the reception module 2 disposed at the maximum leak angle. Therefore, the control module 9 includes a reference crest value storage module 9a that stores a value of a reference crest value.

Figure 2:
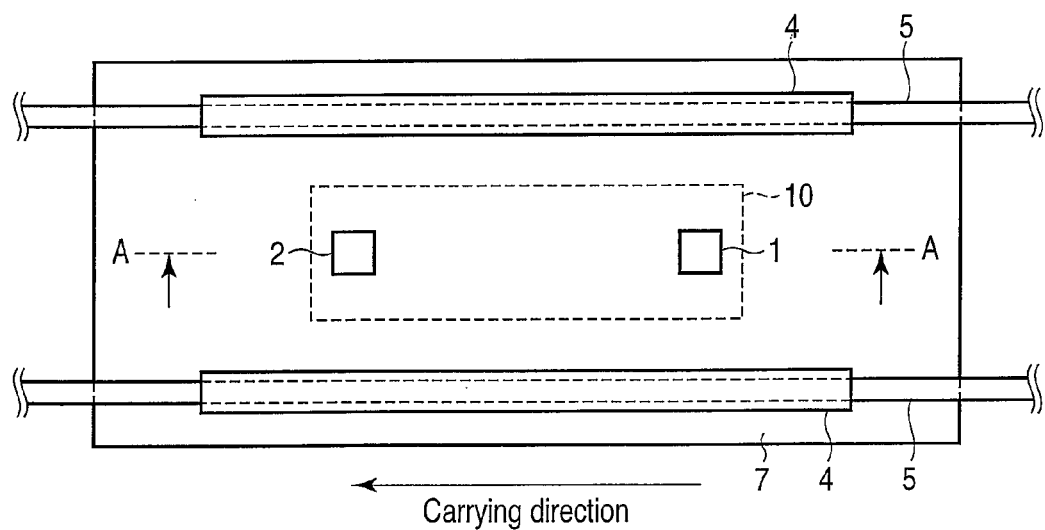
FIG. 2 is an explanatory view for explaining a structural example of the stiffness detector depicted in FIG. 1.

FIG. 2 is a view showing the stiffness detector 10 depicted in FIG. 1 from above.

As shown in FIG. 2, the stiffness detector 10 includes the transmission module 1 and the reception module 2 disposed alongside in the carrying direction of the paper sheet 7. The reception module 2 receives the leaky waves of the Lamb waves excited in the paper sheet 7 by the ultrasonic waves emitted from the transmission module 1.

FIG. 3 is a cross-sectional view of the stiffness detector 10 taken along a line AA in FIG. 2.

As shown in FIG. 3, the paper sheet 7 is carried by the carrying belts 5 bent by the guide plate 4 in a state that it is bent with a predetermined curvature. For example, the paper sheet 7 is bent with a curvature corresponding to an arc of a circle having a radius R and carried.

For example, as shown in FIG. 4, the transmission module 1 and the reception module 2 include vibration planes 11 and 21, respectively. The vibration planes 11 and 12 are displaced in accordance with an applied voltage. Further, each of the vibration planes 11 and 21 generates a voltage in accordance with the displacement of the plane. In this embodiment, it is assumed that the transmission module 1 emits acoustic waves in a direction orthogonal to the vibration plane 11 from a gravity point M1 of the vibration plane 11. Furthermore, it is assumed that the reception module 2 receives the acoustic waves that enter a gravity point M2 of the vibration plane 21 in a direction orthogonal to the vibration plane 21.

The transmission module 1 emits the acoustic waves from the gravity point M1 of the vibration plane 11 to excite the Lamb waves in the paper sheet 7. It is to be noted that a point at which the acoustic waves emitted from the transmission module 1 enter the paper sheet 7 (an incidence point) is determined as I. Moreover, the reception module 2 generates a voltage based on the acoustic waves (the leaky waves) which are emitted from a point D (a detection point D) on the paper sheet 7 and enter the gravity point M2 of the vibration plane 21 in a direction orthogonal to the vibration plane 21, and outputs the generated voltage to the control module 9.

It is assumed that a distance between the incidence point I and the detection point D in the horizontal direction is L. Additionally, an intermediate point of the point I and the point D on the paper sheet 7 is a point P. Further, a point at which a line vertical to the surface of the paper sheet 7 at the point P, a line vertical to the surface of the paper sheet 7 at the point I, and a line vertical to the surface of the paper sheet 7 at the point D cross each other is determined as O. Furthermore, each of a distance between the point O and the point P, a distance between the point O and the point I, and a distance between the point O and the point D is determined as R. Moreover, an angle formed between a line M1I and a line OI is θ1 and an angle formed between a line M2D and a line OD is θ2.

A distance between a line OP and the gravity point M1 in the horizontal direction is determined as L/2. Additionally, a distance between the line OP and the gravity point M2 in the horizontal direction is L/2. In this case, an output direction of the acoustic waves from the transmission module 1 is parallel to the incidence direction of the acoustic waves with respect to the reception module 2. That is, the vibration plane 11 and the vibration plane 21 are parallel to each other. Further, in this case, the angle θ1 is equal to the angle θ2.

Setting the position of the transmission module 1 and the position of the reception module 2 as described above enables representing the radius R of the circle corresponding to the curvature of the paper sheet 7 by the following Expression 3.

$$R = \frac{L}{2\sin\theta_1} \quad \text{(Expression 3)}$$

For example, when the acoustic waves enter the paper sheet 7 from the transmission module 1 at the incidence point I at the optimum incidence angle θ, θ=θ1=θ2 is achieved. In this case, the radius R can be represented by the following Expression 4.

$$R = \frac{L \cdot Cs}{2 \cdot Ca} \quad \text{(Expression 4)}$$

As described above, a curvature of the paper sheet 7 can be determined in accordance with an incidence angle θ1 and an output angle θ2 of the acoustic waves with respect to the paper sheet 7 and the distance L between the incidence point I and the detection point D in the horizontal direction. Further, adjusting the curvature of the paper sheet 7 and the distance L between the incidence angle I and the detection point D in the horizontal direction enables determining the incidence angle θ1 and the output angle θ2 of the acoustic waves with respect to the paper sheet 7.

When the distance L between the incidence point I and the detection point D in the horizontal direction is set to the minimum distance insofar as the reception module 2 can receive the Lamb waves and a sufficient S/N ratio can be assured, the stiffness detector 10 can be arranged compactly.

Furthermore, when the above-described arrangement is adopted, the output direction of the acoustic waves from the transmission module 1 can be set in parallel with the incidence direction of the acoustic waves with respect to the reception module 2. Therefore, crosstalk can be avoided.

Figure 5:
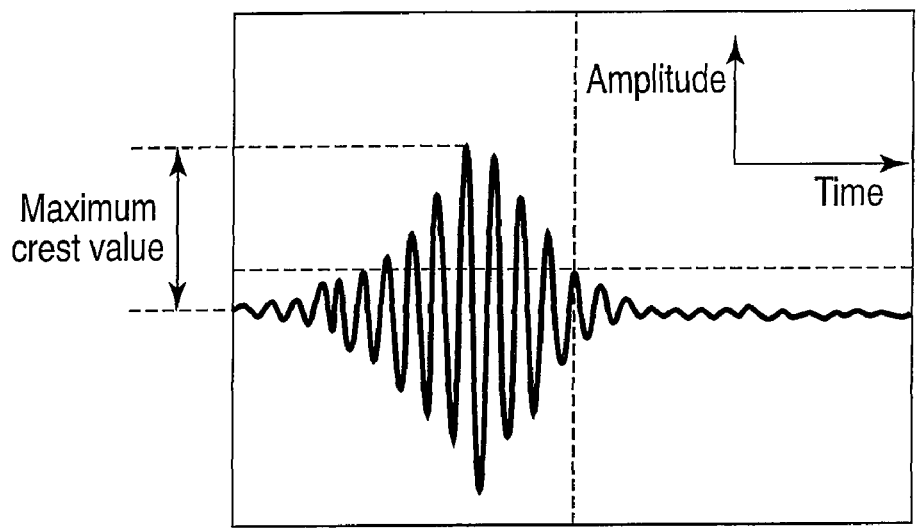
FIG. 5 is an explanatory view for explaining an example of a waveform received by the reception module.
Figure 6:
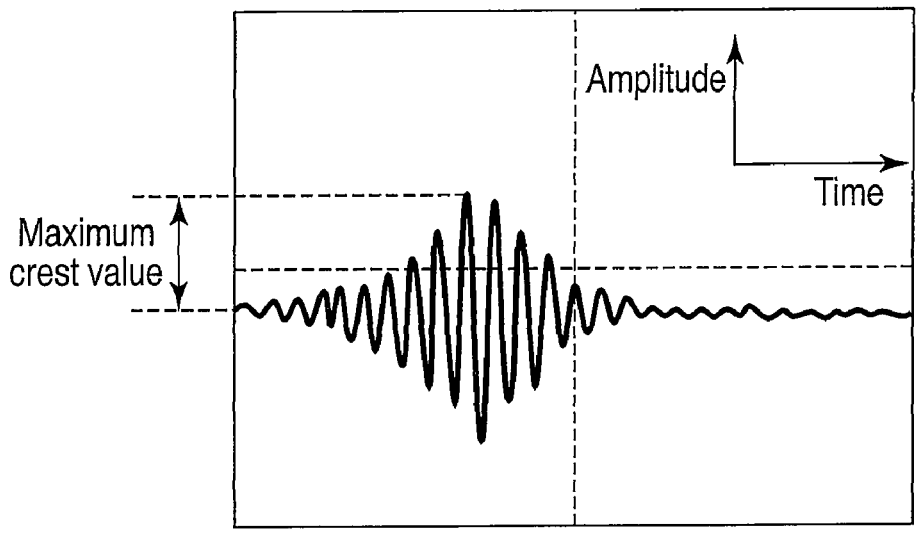
FIG. 6 is an explanatory view for explaining an example of a waveform received by the reception module.

FIGS. 5 to 7 are views each showing a waveform of waves received by the reception module 2.

FIG. 5 is an explanatory view for explaining an example of a result of examination conducted with respect to the non-fatigued paper sheet 7. FIG. 6 is an explanatory view for explaining an example of a result of examination conducted with respect to the fatigued paper sheet 7. FIG. 7 is an explanatory view for explaining an example of a result of examination conducted with respect to the paper sheet 7 that is further fatigued as compared with example depicted in FIG. 6.

In each graph depicted in FIGS. 5 to 7, an abscissa represents a time, and an ordinate represents an amplitude of waves. As shown in FIGS. 5 to 7, the waveform received from the non-fatigued paper sheet 7 has the largest amplitude (a maximum crest value). Furthermore, as shown in FIGS. 6 and 7, the maximum crest value is reduced as a degree of fatigue increases.

The control module 9 in the stiffness detector 10 judges wear of the paper sheet 7 based on the maximum crest value of the waveform received by the reception module 2. That is, the control module 9 functions as a judgment module. The control module 9 specifies the maximum crest value based on an output from the reception module 2. The control module 9 compares a reference crest value previously stored in the reference crest value storage module 9a with the specified maximum crest value. That is, the control module 9 functions as a comparison module.

When the specified maximum crest value is equal to or above the reference crest value stored in the reference crest value storage module 9a, the control module 9 determines that the paper sheet 7 is an unimpaired sheet. Moreover, when the specified maximum crest value is less than the reference crest value stored in the reference crest value storage module 9a, the control module 9 determines that the paper sheet 7 is an impaired sheet.

FIG. 8 is a flowchart for explaining an operation of the stiffness detector 10. It is to be noted that installation angles of the transmission module 1 and the reception module 2 are preset in accordance with a medium to be examined.

When the control module 9 in the stiffness detector 10 has detected the paper sheet 7, it applies a pulse signal to the transmission module 1 (a step S11). As a result, the transmission module 1 emits acoustic waves toward the paper sheet 7 at the same time. The acoustic waves that have entered the paper sheet 7 excite Lamb waves in a medium of the paper sheet 7. The excited Lamb waves are propagated through the paper sheet 7 and leak from the paper sheet 7 during propagation, thereby emitting leaky waves.

The reception module 2 in the stiffness detector 10 receives the leaky waves of the Lamb waves exiting from the paper sheet 7 (a step S12). The control module 9 specifies a maximum crest value based on a waveform received by the reception module 2 (a step S13).

The control module 9 judges whether the specified maximum crest value is less than the reference value (a step S14). That is, the control module 9 compares the maximum crest value with the reference crest value stored in the reference crest value storage module 9a to judge whether the maximum crest value is less than the reference crest value.

When the maximum crest value is determined to be less than the reference value at the step S14 (the step S14, YES), the control module 9 determines that the paper sheet 7 is an impaired sheet (a step S15). That is, the control module 9 determines that the paper sheet 7 is not appropriate for recirculation since the paper sheet 7 has a high degree of fatigue.

When the maximum crest value is determined to be equal to or above the reference value at the step S14 (the step S14, NO), the control module 9 determines that the paper sheet 7 is an unimpaired sheet (a step S16). That is, the control module 9 determines that the paper sheet 7 is appropriate for recirculation since the paper sheet 7 has a low degree of fatigue.

As described above, the stiffness detector 10 according to this embodiment separates the transmission module 1 from the reception module 2 to interpose a predetermined gap therebetween and arranges them in such a manner that the output direction of the acoustic waves from the transmission module 1 becomes parallel to the incidence direction of the acoustic waves with respect to the reception module 2. The stiffness detector 10 bends and carries the paper sheet 7 in such a manner that the incidence angle θ1 of the acoustic waves with respect to the paper sheet 7 from the transmission module 1 and the output angle θ2 of the acoustic waves emitted toward the reception module 2 from the paper sheet 7 can be predetermined angles.

The stiffness detector 10 uses the transmission module 1 arranged as described above to apply acoustic waves with respect to the carried paper sheet 7. The stiffness detector 10 uses the reception module 2 to receive the leaky waves of the Lamb waves emitted from the paper sheet 7. The control module 9 in the stiffness detector 10 specifies the maximum crest value based on the received waveform and judges whether the paper sheet 7 is an unimpaired sheet based on the previously stored reference crest value and the specified maximum crest value. As a result, it is possible to judge whether the paper sheet 7 can be recirculated as the unimpaired sheet in accordance with a degree of fatigue of the paper sheet 7.

As a result, it is possible to provide the stiffness detector that can highly accurately detect the stiffness of paper sheets in a compact configuration, the stiffness detection method and the paper sheet processor including the stiffness detector.

It is to be noted that the guide plate 4 bends the paper sheet 7 with the curvature corresponding to the arc of the circle having the radius R in the above description of the following embodiment, but the present invention is not restricted thereto. The paper sheet 7 can be bent in any shape as long as the arc can provide the relationship that the acoustic waves exiting from the gravity point M1 of the vibration plane 11 of the transmission module 1 enter the surface of the paper sheet 7 at a predetermined angle at the incidence point I at which the acoustic waves enter, the line formed by the gravity point M2 of the vibration plane 21 of the reception module 2 and the detection point D and the line vertical to the surface of the paper sheet 7 at the detection point D form a predetermined angle, and the line formed by the gravity point M1 and the incidence point I and the line formed by the gravity point M2 and the detection point D are parallel to each other. For example, curvatures of the paper sheets 7 do not have to be uniform.

Further, in the foregoing embodiment, although the guide plate 4 having a predetermined curvature bends the conveying belts 5 in the above description, the present invention is not restricted thereto. Any guide plate can be used as long as it has the predetermined curvature.

Figure 9:
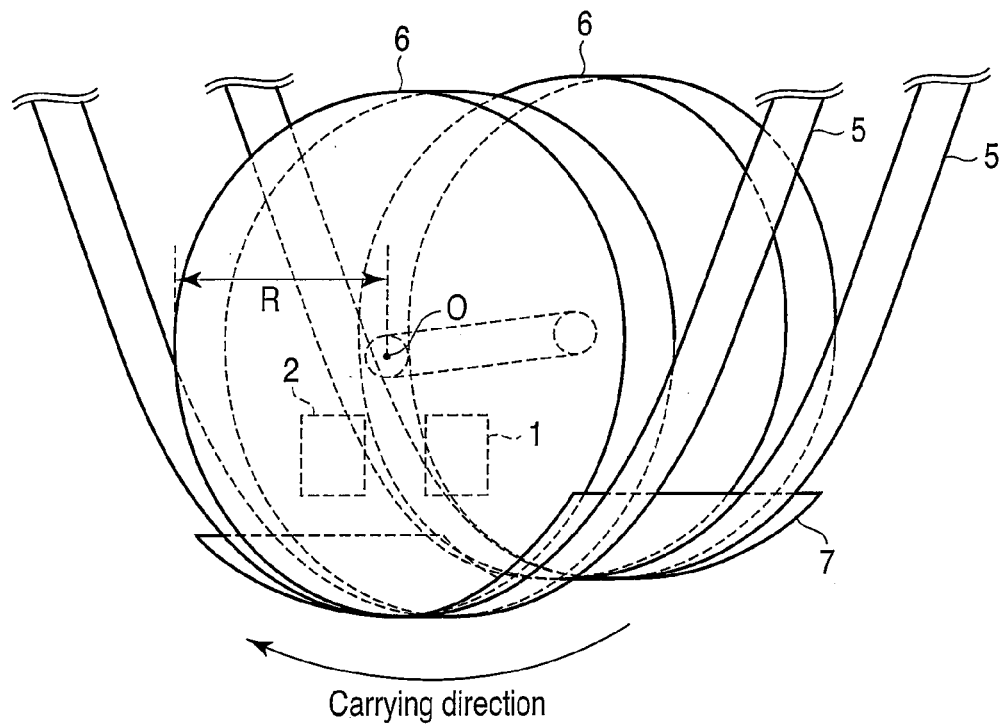
FIG. 9 is an explanatory view for explaining an example of arrangement of each module in the stiffness detector.

FIG. 9 is an explanatory view for explaining a configuration for bending the conveying belts 5 by driving pulleys 6.

As shown in FIG. 9, the stiffness detector 10 includes the driving pulleys 6 each having a radius R along the conveying belts 5. Furthermore, arranging the transmission module 1 and the reception module 2 between the driving pulleys 6 enables satisfying the same installation conditions as those in the example depicted in FIG. 3.

Figure 10:
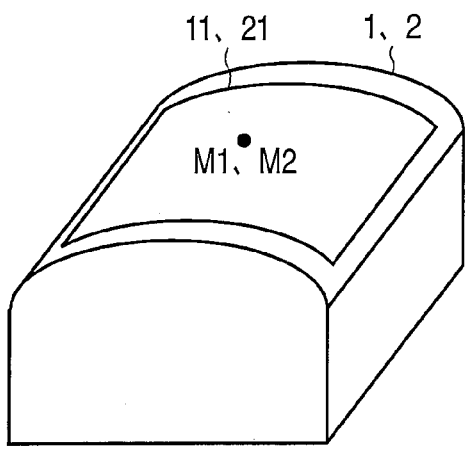
FIG. 10 is an explanatory view for explaining another example of the configuration of the transmission module and the reception module in the stiffness detector.

Moreover, in the foregoing embodiment, although the vibration planes 11 and 21 of the transmission module 1 and the reception module 2 are flat planes in the above description, the present invention is not restricted to this configuration. For example, as shown in FIG. 10, each of the vibration planes 11 and 12 may be a curved plane like the paper sheet 7. For example, each of the vibration planes 11 and 21 has the same curvature as that of the paper sheet 7. Additionally, for example, each of the vibration planes 11 and 21 may include a sound collection lens and others.

Another embodiment of the stiffness detector 10 will now be described.

FIG. 11 is an explanatory view for explaining a structural example of a stiffness detector 10 according to another embodiment. It is to be noted that like reference numerals denote like structures in the stiffness detector 10 depicted in FIG. 1 to omit a detailed description thereof.

As depicted in FIG. 11, the stiffness detector 10 according to this embodiment includes a transmission module 1, a reception module 2 and a guide plate 4. Further, like the embodiment depicted in FIG. 1, the stiffness detector 10 includes a control module 9 (not shown) that controls the transmission module 1 and the reception module 2. The transmission module 1, the reception module 2 and the guide plate 4 are disposed on one surface side of a paper sheet 7 to be carried.

The transmission module 1 includes a plurality of transmission modules (transducers) 1A, 1B and 1C. Furthermore, the reception module 2 includes a plurality of reception modules (reception sensors) 2A, 2B and 2C.

As depicted in FIG. 11, the transmission modules 1A, 1B and 1C are aligned and disposed in a direction orthogonal to a carrying direction of the paper sheet 7. Moreover, the reception modules 2A, 2B and 2C are aligned and disposed in the direction orthogonal to the carrying direction of the paper sheet 7.

A pair of the transmission module 1A and the reception module 2A, a pair of the transmission module 1B and the reception module 2B and a pair of the transmission module 1C and the reception module 2C are provided in association with each other, respectively. That is, the reception module 2A receives leaky waves of Lamb waves excited by ultrasonic waves emitted from the transmission module 1A. Further, the reception module 2B receives the leaky waves of the Lamb waves excited by the ultrasonic waves emitted from the transmission module 1B. Furthermore, the reception module 2C receives the leaky waves of the Lamb waves excited by the ultrasonic waves emitted from the transmission module 1C.

In this embodiment, a maximum leak angle of the non-fatigued paper sheet 7 is determined as a reference angle, and the reception modules 2A, 2B and 2C are disposed at a plurality of different angles. In this case, for example, the reception module 2A is disposed at an angle corresponding to the reference angle+N degrees, the reception module 2B is disposed at the reference angle, and the reception module 2C is disposed at an angle corresponding to the reference angle−M degrees.

It is to be noted that the description will be given on the assumption that the reference angle of the non-fatigued paper sheet 7 is 27 degrees in this embodiment. Moreover, the explanation will be given on the assumption that N=M=1 is achieved.

Figure 13:
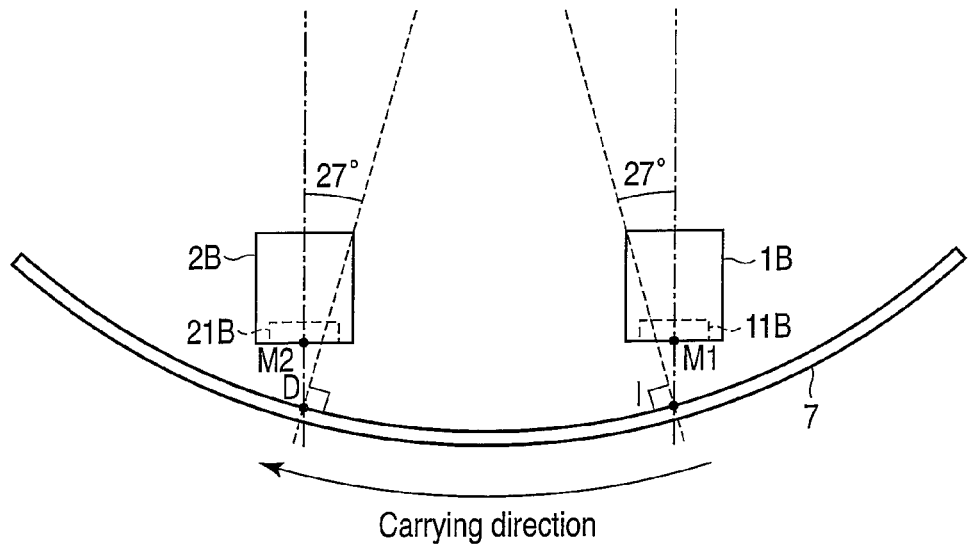
FIG. 13 is an explanatory view for explaining an example of arrangement of each module in the stiffness detector depicted in FIG. 11.
Figure 14:
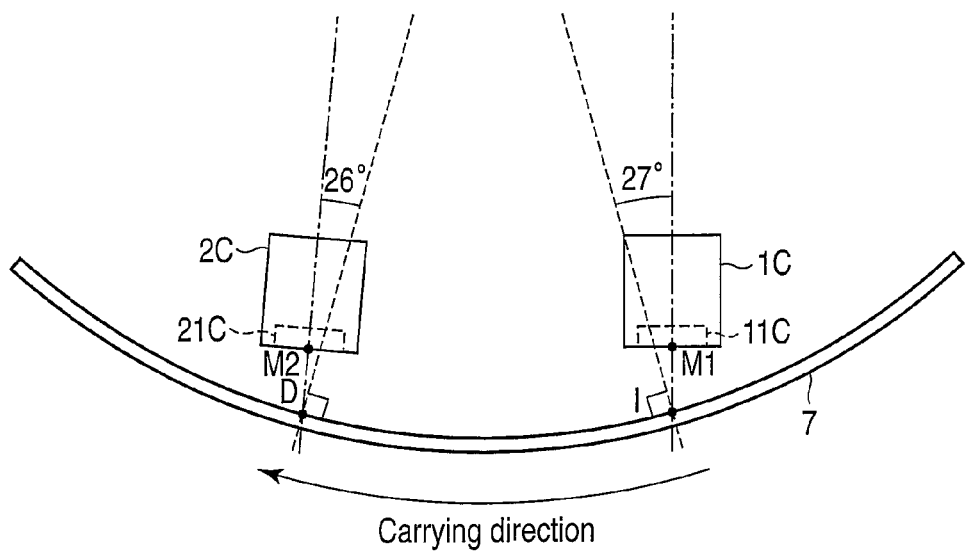
FIG. 14 is an explanatory view for explaining an example of arrangement of each module in the stiffness detector depicted in FIG. 11.

FIGS. 12 to 14 are cross-sectional views for explaining arrangement of the transmission module 1 and the reception module 2 in the stiffness detector 10 depicted in FIG. 11. FIG. 12 is a cross-sectional view of the stiffness detector 10 in FIG. 11 taken along a line AA. Moreover, FIG. 13 is a cross-sectional view of the stiffness detector 10 in FIG. 11 taken along a line BB. Additionally, FIG. 14 is a cross-sectional view of the stiffness detector 10 in FIG. 11 taken along a line CC.

As shown in FIG. 12, the transmission module 1A is installed in such a manner that a traveling direction of acoustic waves that enter an incidence point I of the paper sheet 7 from a gravity point M1 of a vibration plane 11A and a line vertical to the surface of the paper sheet 7 at the incidence point I form an angle of 27 degrees (a reference angle). Additionally, the reception module 2A is installed in such a manner that a traveling direction of the acoustic waves that enter a gravity point M2 of a vibration plane 21A from a detection point D and a line vertical to the surface of the paper sheet 7 at the detection point D form an angle of 28 degrees (the reference angle+1 degree).

Further, as shown in FIG. 13, the transmission module 1B is installed in such a manner that a traveling direction of the acoustic waves that enter the incidence point I of the paper sheet 7 from a gravity point M1 of a vibration plane 11B and the line vertical to the surface of the paper sheet 7 at the incidence point I form an angle of 27 degrees (the reference angle). Furthermore, the reception module 2B is installed in such a manner that a traveling direction of the acoustic waves that enter a gravity point M2 of the vibration plane 21B from the detection point D and the line vertical to the surface of the paper sheet 7 at the detection point D form an angle of 27 degrees (the reference angle). It is to be noted that the traveling direction of the acoustic waves emitted from the transmission module 1 becomes parallel to the traveling direction of the acoustic waves that enter the reception module 2.

Furthermore, as shown in FIG. 14, the transmission module 1C is disposed in such a manner that a traveling direction of the acoustic waves that enter the incidence point I of the paper sheet 7 from a gravity point M1 of a vibration plane 11C and the line vertical to the surface of the paper sheet 7 at the incidence point I form an angle of 27 degrees (the reference angle). Moreover, the reception module 2C is installed in such a manner that a traveling direction of the acoustic waves that enter a gravity point M2 of the vibration plane 21C from the detection point D and the line vertical to the surface of the paper sheet 7 at the detection point D form an angle of 26 degrees (the reference angle−1 degree).

Arranging the reception modules 2A, 2B and 2C as described above enables detecting the leaky waves of the Lamb waves propagated through the paper sheet 7 at different angles.

Each of FIGS. 15 to 17 is an explanatory view for explaining a relationship between a maximum crest value of a waveform received by each reception module 2A, 2B or 2C in the stiffness detector 10 depicted in FIG. 11 and an installation angle.

FIG. 15 is a view for showing a relationship between a maximum crest value in a result of examination conducted with respect to the non-fatigued paper sheet 7 and an installation angle of the reception module 2. FIG. 16 is a view showing a relationship between a maximum crest value in a result of examination conducted with respect to the fatigued paper sheet 7 and an installation angle of the reception module 2. FIG. 17 is a view showing a relationship between a maximum crest value in a result of examination conducted with respect to the paper sheet 7 that is more fatigued than the paper sheet 7 in the example depicted in FIG. 16 and an installation angle of the reception module 2.

The control module 9 in the stiffness detector 10 judges a degree of fatigue and wear of the paper sheet 7 based on a relationship between a maximum crest value of a waveform received by the reception module 2 and an installation angle of the reception module 2. That is, the control module 9 functions as a judgment module. The control module 9 specifies an angle at which a leak amount becomes maximum, i.e., the installation angle of the reception module 2 that has detected the largest maximum crest value as a maximum leak angle. The control unit 9 compares the specified maximum leak angle with a reference angle previously determined based on characteristics of the paper sheet 7. That is, the control module 9 functions as an angle comparison module.

When the maximum leak angle coincides with the reference angle, the control module 9 determines that the paper sheet 7 is not fatigued. Additionally, when the maximum leak angle does not coincide with the reference angle, the control module 9 determines that the paper sheet 7 is fatigued.

As shown in FIG. 15, the reception module 2B installed with respect to the paper sheet 7 at the angle of 27 degrees (the reference angle) detects the largest maximum crest angle. In this case, the control module 9 specifies the installation angle of 27 degrees of the reception module 2B as the maximum leak angle. When the maximum leak angle coincides with the reference angle, the control module 9 determines that the paper sheet 7 is not fatigued.

Further, as shown in FIGS. 16 and 17, the reception module 2C installed at the angle of 26 degrees (an angle that is not the reference angle) with respect to the paper sheet 7 detects the largest maximum crest value. In this case, the control module 9 specifies the installation angle of 26 degrees of the reception module 2C as the maximum leak angle. When the maximum leak angle does not coincide with the reference angle, the control module 9 determines that the paper sheet 7 is fatigued.

Furthermore, the control module 9 compares the maximum crest value having the largest value with a reference crest value stored in a reference crest value storage module 9a. When the maximum crest value having the largest value is equal to or above the reference crest value stored in the reference crest value storage module 9a, the control module 9 determines that the paper sheet 7 is an unimpaired sheet. Moreover, when the maximum crest value having the largest value is less than the reference crest value stored in the reference crest value storage module 9a, the control module 9 determines that the paper sheet 7 is an impaired sheet.

As described above, the stiffness detector 10 according to this embodiment applies acoustic waves with respect to the paper sheet 7. In the stiffness detector 10, the reception modules 2 arranged at the plurality of angles receive the leaky waves of the Lamb waves emitted from the paper sheet 7. The control module 9 in the stiffness detector 10 specifies the maximum crest value and the maximum leak angle based on the received waveform.

The control module 9 compares the previously determined reference angle with the specified maximum leak angle to judge whether the paper sheet 7 is a fatigued sheet. Moreover, the control module 9 compares the previously stored reference crest value with the specified maximum crest value to judge whether the paper sheet 7 is an unimpaired sheet. As a result, a degree of fatigue of the paper sheet 7 can be specified. Additionally, whether the paper sheet 7 can be recirculated as an unimpaired sheet can be judged in accordance with the degree of fatigue of the paper sheet 7.

As a result, the stiffness detector that can highly accurately detect the stiffness of paper sheets in a compact configuration, the stiffness detection method and the paper sheet processor including the stiffness detector can be provided.

It is to be noted that the three transmission modules 3 are provided in association with the three reception modules in the foregoing embodiment, but one transmission module can suffice. Moreover, although the transmission module 1 is installed at the optimum incidence angle with respect to the paper sheet 7 in the above description, the present invention is not restricted thereto. The transmission module 1 can be installed at any angle as long as the installation angle of the transmission module 1 is an angle at which the Lamb waves can be excited in the paper sheet 7.

A paper sheet processor including the stiffness detector 10 will now be described.

FIG. 18 is an explanatory view for explaining an appearance of the paper sheet processor according to an embodiment.

As shown in FIG. 18, the paper sheet processor 100 exteriorly includes an injection module 112, an operation module 136, an operation display module 137, a door 138, an ejection opening 139 and a keyboard 140.

The injection module 112 is configured to put in the paper sheet 7. The injection module 112 receives the stacked paper sheets 7 in bulk. The operation module 136 accepts input of various operations performed by an operator. The operation display module 137 displays various kinds of operation guides, processing results and others for the operator. It is to be noted that the operation display module 137 may be configured as a touch panel. In this case, the paper sheet processor 100 detects input of various operations based on buttons displayed in the operation display module 137 and an operation performed by the operator with respect to the operation display module 137.

The door 138 is a door which is utilized to open/close an injection opening of the injection module 112. The ejection opening 139 is configured to take out the paper sheets 7 from an accumulation module where the paper sheets 7 determined to be inappropriate for recirculation by the paper sheet processor 100 are stacked. The keyboard 140 functions as an input module that accepts input of various operations performed by the operator.

FIG. 19 is an explanatory view for explaining a structural example of the paper sheet processor 100 depicted in FIG. 18.

The paper sheet processor 100 includes the injection module 112, an ejection module 113, an adsorption roller 114, a carrier path 115, an examination module 116, gates 120 to 125, a rejection carrier path 126, a rejection accumulation module 127, accumulation/bundling modules 128 to 131, a cutting module 133 and a stacker 134. Further, the paper sheet processor 100 includes a main control module 151. The main control module 151 integrally controls operations of the respective modules in the paper sheet processor 100.

The ejection module 113 is provided above the injection module. The ejection module 113 includes the adsorption roller 114. The adsorption roller 114 is provided to be in contact with an upper end of the paper sheet 7 set in the injection module 112 in an accumulating direction. That is, when the adsorption roller 114 rotates, it takes in the papers sheets 7 set in the injection module 112 one by one from the upper end in the accumulating direction into the processor. For example, when the adsorption roller 114 functions to take out one paper sheet 7 every time it makes one revolution. As a result, the adsorption roller 114 takes out the paper sheets 7 at a fixed pitch. The paper sheets 7 taken in by the adsorption roller 114 are introduced into the carrier path 115.

The carrier path 115 is carrying means for carrying the paper sheets 7 to the respective modules in the paper sheet processor 100. The carrier path 115 includes the conveying belts 5, non-illustrated driving pulleys and others. The carrier path 115 uses non-illustrated driving motor and driving pulleys to operate the carrying belts 5. The carrier path 115 carries the paper sheets 7 taken in by the adsorption roller 114 at a fixed speed by using the conveying belts 5. It is to be noted that a side of the carrier path 115 close to the ejection module 113 is an upstream side and a side of the same close to the stacker 134 is a downstream side in the following description.

The examination module 116 is provided on the carrier path 115 extending from the ejection module 113. The examination module 116 includes an image reader 117, an image reader 118, a stiffness detector 10 and a thickness examiner 119. The examination module 116 detects optical characteristic information, mechanical characteristics and magnetic feature information of the paper sheet 7. As a result, the paper sheet processor 100 examines a type, fouling damages, front and back sides, authenticity and others of the paper sheet 7.

The image readers 117 and 118 are provided to face each other with the carrier path 115 interposed therebetween. The image readers 117 and 118 read images on both surfaces of the paper sheet 7 carried through the carrier path 115. Each of the image readers 117 and 118 includes a charge coupled device (CCD) camera. The paper sheet processor 100 acquires pattern images on the front surface and the back surface of the paper sheet 7 based on images acquired by the image readers 117 and 118.

The image readers 117 and 118 temporarily stores the read images in a non-illustrated memory in the examination module 116. The paper sheet processor 100 displays the images stored in this memory in the operation display module 137 in accordance with operation inputs.

The stiffness detector 10 detects mechanical characteristics of the paper sheet 7 as described above. As a result, the stiffness detector 10 judges whether the paper sheet 7 is an impaired sheet that is fatigued and cannot be recirculated or whether it is an unimpaired sheet that can be recirculated. It is to be noted that, as shown in the drawing, the stiffness detector 10 bends the conveying belts 5. As a result, the stiffness detector 10 can bend the paper sheet 7 to be carried near the stiffness detector 10.

The thickness examination module 119 examines a thickness of the paper sheet 7 carried through the carrier path 115. For example, when the detected thickness is equal to or above a specified value, the paper sheet processor 100 detects a state that the two paper sheets 7 have been taken at the same time.

Furthermore, the examination module 116 includes a non-illustrated magnetic sensor and others. The magnetic sensor detects magnetic characteristic information of the paper sheet 7.

The main control module 151 judges whether the paper sheet 7 is an unimpaired sheet, an impaired sheet or a rejected sheet based on detection results obtained from the image readers 117 and 118, the stiffness detector 10, the thickness examination module 119, the magnetic sensor and others.

The paper sheet processor 100 carries the paper sheet 7 determined as an unimpaired sheet to the accumulation/bundling modules 128 to 131. Furthermore, the paper sheet processor 100 carries the paper sheet 7 determined as an impaired sheet to the cutting module 133. The cutting module 133 cuts the carried impaired sheet. It is to be noted that the paper sheet processor 100 may carry the impaired sheet to the stacker 134 to be stacked. The stacker 134 performs sealing every time the number of the stacked impaired sheet reaches, e.g., 100.

The rejected sheet is the paper sheet 7 which does not correspond to the unimpaired sheet and the impaired sheet. The paper sheet processor 100 carries the paper sheet 7 determined as the rejected sheet to the rejection accumulation module 127. The rejected sheet includes, e.g., an abnormally carried sheet such as a sheet taken with the other note at the same time, a defective sheet such as a folded or worn sheet, and an unrecognizable sheet such as an unapplied note type or a false sheet.

The gates 120 to 125 are sequentially arranged on the carrier path 115 on the downstream side of the examination module 116. Each of the gates 120 to 125 is controlled by the main control module 151. The main control module 151 controls operations of the respective gates 120 to 125 based on a result of examination executed by the examination module 116. As a result, the main control module 151 controls to carry the paper sheet 7 that is being carried through the carrier path 115 to a predetermined processing module.

The gate 120 arranged right behind the examination module 116 branches the carrier path 115 to the rejection carrier path 126. That is, the gate 120 is switched in such a manner that a rejected sheet determined as a non-genuine sheet as a result of examination executed by the examination module 116 or a non-testable sheet that cannot be subjected to examination by the examination module 116 is carried to the rejection carrier path 126.

The rejection accumulation module (a rejection module) 127 is provided at a trailing end of the rejection carrier path 126. The rejection accumulation module 127 accumulates the above-described rejected sheet or non-testable sheet while keeping a posture when taken out from the rejection module 113. The paper sheet 7 accumulated in the rejection accumulation module 127 can be taken out from the ejection opening 139.

Further, the accumulation/bundling modules 128 to 131 (which are generically called an accumulation/bundling module 132) are provided at branch destinations from the gates 121 to 124, respectively. The paper sheets 7 which can be recirculated are classified in accordance with a type and a front or back surface and then accumulated in the accumulation/bundling module 132. The accumulation/bundling module 132 bundles a predetermined number of the accumulated paper sheets 7 at a time to be stored. Furthermore, the paper sheet processor 100 uses a non-illustrated high-bulk bundling module to accumulate and bundle a plurality of bundles each including the predetermined number of paper sheets 7.

The cutting module 133 is arranged at a branch destination from the gate 125. The cutting module 133 cuts and accommodates the paper sheets 7. The paper sheets 7 carried to the gate 125 are the proper paper sheet 7 and the paper sheet 7 (an impaired sheet) determined as being unable to be recirculated.

Moreover, the stacker 134 is arranged at a destination of the other carrier path branching from the gate 125. The main control module 151 controls the gate 125 to carry the paper sheet 7 to the cutting module 133 when an impaired sheet cutting mode is selected. Additionally, the main control module 151 controls the gate 125 to carry the paper sheet 7 to the stacker 134 when the impaired sheet cutting mode is not selected.

It is to be noted that the main control module 151 sequentially stores the number of the paper sheets 7 accumulated in the accumulation/bundling module 132, the number of the paper sheets 7 cut by the cutting module 133 and identifying information.

Figure 20:
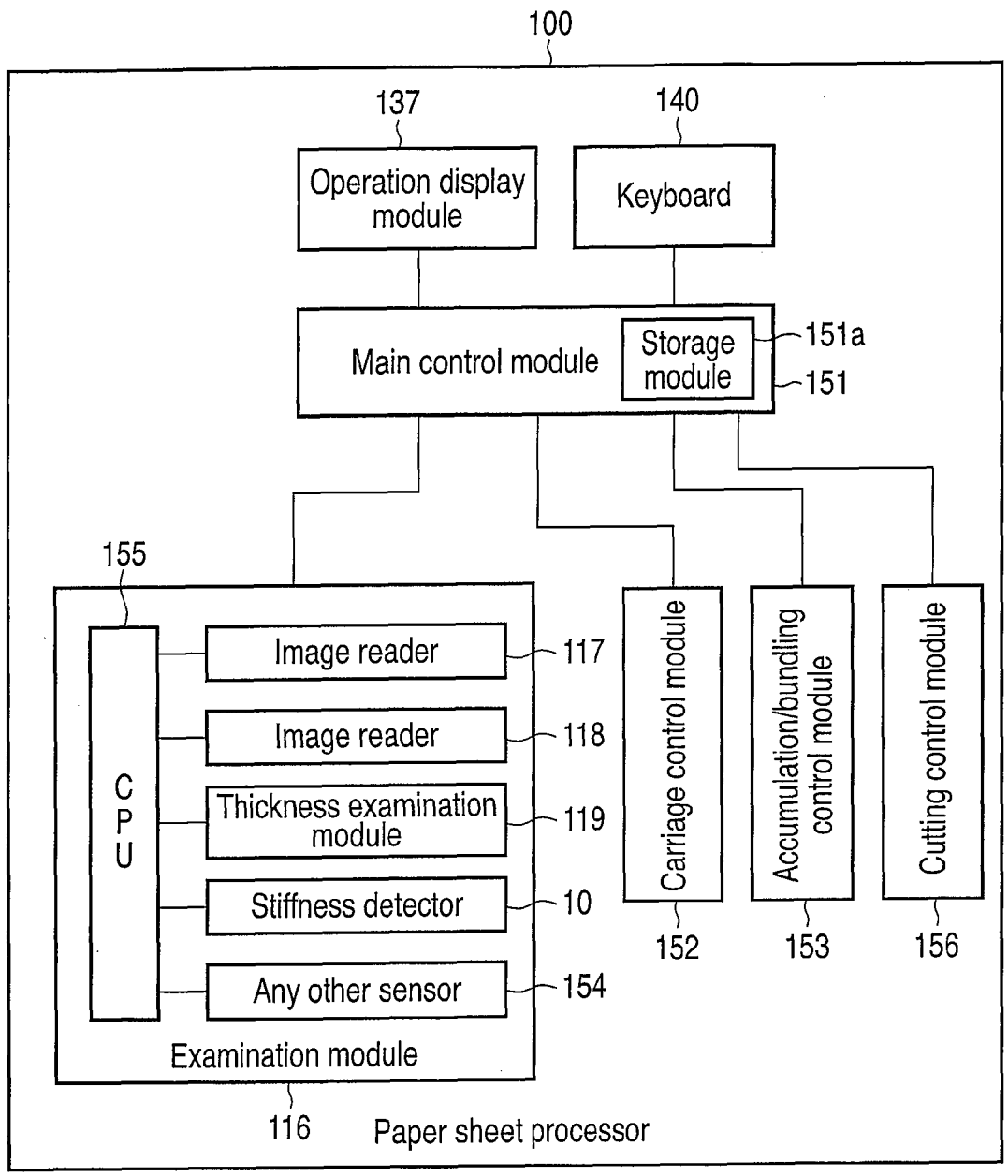
FIG. 20 is a block diagram for explaining a structural example of a control system of the paper sheet processor depicted in FIGS. 18 and 19.

FIG. 20 is a block diagram for explaining a structural example of a control system in the paper sheet processor 100 depicted in FIGS. 18 and 19.

The paper sheet processor 100 includes the main control module 151, the examination module 116, the carriage control module 152, an accumulation/bundling control module 153, a cutting control module 156, the operation display module 137, the keyboard 140 and others.

The main control module 151 controls the entire paper sheet processor 100. The main control module 151 controls the carriage control module 152 and the accumulation/bundling control module 153 based on an operation input through the operation display module 137 and a result of examination executed by the examination module 116.

For example, an operator uses the operation display module 137 or the keyboard 140 to input a sheet type, the number, a wear judgment level, a name of a supply source, a processing method and others of the paper sheet 7 to be processed.

The examination module 116 includes the image readers 117 and 118, the thickness examination module 119, the stiffness detector 10, any other sensor 154 and a CPU 155.

The image readers 117 and 118 read images on both surfaces of the paper sheet 7 carried through the carrier path 115. Each of the image readers 117 and 118 includes a light receiving element such as a CCD and an optical system. Each of the image readers 117 and 118 projects light onto the carried paper sheet 7 and receives reflected light or transmitted light by using the optical system. Each of the imager readers 117 and 118 forms an image of the light received through the optical system onto the CCD to acquire an electric signal (an image).

The main control module 151 stores an image that serves as a reference for the paper sheet 7 (a reference image) in a storage module 151a in advance. The main control module 151 compares an image acquired from the paper sheet 7 with the reference image stored in the storage module 151a to make a wear judgment and a true-false judgment of the sheet.

As described above, the stiffness detector 10 uses the transmission module 1 to apply acoustic waves at a predetermined angle to the carried paper sheet 7 that is carried in a bent state. The stiffness detector 10 uses the reception module arranged at a predetermined angle with respect to the paper sheet 7 to receive leaky waves of Lamb waves emitted from the paper sheet 7. The control module 9 of the stiffness detector 10 specifies a maximum crest value based on a waveform received by the reception module 2.

The control module 9 compares a reference crest value stored in the reference crest value storage module 9a with the specified maximum crest value to judge whether the paper sheet 7 is an unimpaired sheet. As a result, the stiffness detector 10 can judge whether the paper sheet 7 can be recirculated as an unimpaired sheet.

The thickness examination module 119 examines a thickness of the paper sheet 7 carried through the carrier path 115. Any other sensor 154 is, e.g., a magnetic sensor. The magnetic sensor detects magnetic characteristic information from the paper sheet 7 carried through the carrier path 115.

The CPU 155 judges a type, wear, front and back surfaces, authenticity and others of the paper sheet 7 carried through the carrier path 115 based on results of examination executed by the image readers 117 and 118, the thickness examination module 119, the stiffness detector 10, any other sensor 154 and others.

The carriage control module 152 controls the ejection module 113, the carrier path 115, the rejection carrier path 126 and the gates 120 to 125 under control of the main control module 151. As a result, the carriage control module 152 controls fetch and carriage of the paper sheet 7. Furthermore, the carriage control module 152 executes classification processing for classifying the determined paper sheets 7 in accordance with each type. That is, the carriage control module 152 functions as a classification processing module. It is to be noted that the carriage control module 152 performs classification in accordance with each type of the paper sheet 7, but it is not restricted thereto. For example, the paper sheet 7 may be classified and processed in accordance with a degree of fatigue based on an examination result obtained by the stiffness detector 10.

The accumulation/bundling control module 153 controls the rejection accumulation module 127 and the accumulation/bundling modules 128 to 131 under control of the main control module 151. As a result, the accumulation/bundling control module 153 controls accumulation and bundling of the paper sheet 7.

The cutting control module 156 controls operations of the cutting module 133 under control of the main control module 151. As a result, the cutting module 133 cuts the carried paper sheet 7.

As described above, the paper sheet processor 100 including the stiffness detector 10 according to an embodiment of the present invention examines the paper sheet 7 by using the stiffness detector 10. The stiffness detector 10 examines mechanical characteristics of the paper sheet 7 and judges whether the paper sheet 7 can be recirculated. The paper sheet processor 100 can appropriately process the paper sheet 7 based on a judgment result.

Additional advantages and modifications will readily occur to those skilled in the art. Therefore, the invention in its broader aspects is not limited to the specific details and representative embodiments shown and described herein.

Accordingly, various modifications may be made without departing from the spirit or scope of the general inventive concept as defined by the appended claims and their equivalents.

What is claimed is:

1. A stiffness detector comprising:
a bending portion configured to bend a paper sheet to be carried;
a transmission module configured to transmit acoustic waves to an incidence point on an inner surface of the paper sheet which is bent by the bending portion and is carried, thereby exciting Lamb waves, wherein the transmission module is disposed such that the acoustic waves enters the incident point on the inner surface of the paper sheet at a predetermined angle;
a reception module configured to receive leaky waves of the Lamb waves emitted from a detection point on the inner surface of the paper sheet, wherein the reception module is disposed such that an output direction of the acoustic waves is parallel with an incidence direction of the leaky waves entering the reception module; and
a first judgment module configured to specify a maximum crest value based on an output from the reception module and judge whether the paper sheet is an unimpaired sheet based on the specified maximum crest value.

2. The stiffness detector according to claim 1, wherein the bending portion bends the paper sheet in such a manner that an angle formed by a direction in which the acoustic waves transmitted from the transmission module enter the paper sheet and the surface of the paper sheet becomes a reference angle at the incidence point on the paper sheet which the acoustic waves emitted from the transmission module enter.

3. The stiffness detector according to claim 1, wherein the bending portion bends the paper sheet in such a manner that an angle formed by a direction of the acoustic waves emitted from the detection point to enter the reception module and the surface of the paper sheet becomes a reference angle at the detection point on the paper sheet.

4. The stiffness detector according to claim 1, further comprising:
a reference crest value storage module configured to store a reference crest value in advance; and
a crest value comparison module configured to compare the specified maximum crest value with the reference crest value stored in the reference crest value storage module,
wherein the first judgment module judges whether the paper sheet is an unimpaired sheet based on a comparison result obtained from the crest value comparison module.

5. The stiffness detector according to claim 4, wherein the first judgment module determines that the paper sheet is an impaired sheet when the specified maximum crest value is less than the reference crest value stored in the reference crest value storage module as a result of comparison performed by the crest value comparison module.

6. The stiffness detector according to claim 1, wherein the reception module comprises a first reception sensor installed at a reference angle with respect to the surface of the paper sheet, a second reception sensor installed at an angle corresponding to the reference angle+N degrees, and a third reception sensor installed at an angle corresponding to the reference angle−M degrees.

7. The stiffness detector according to claim 6, further comprising a second judgment module configured to specify a maximum leak angle at which a leak amount of the acoustic waves from the paper sheet becomes maximum based on outputs from the plurality of reception sensors in the reception module and to judge a degree of fatigue of the paper sheet based on the specified maximum leak angle.

8. The stiffness detector according to claim 7, wherein the second judgment module determines that the paper sheet is a fatigued paper sheet when the specified maximum leak angle does not coincide with the previously determined reference angle.

9. A stiffness detection method comprising:
transmitting acoustic waves to an incidence point on an inner surface of a paper sheet which is bent and carried, thereby exciting Lamb waves, the acoustic waves entering the inner surface of the paper sheet at a predetermined angle;
receiving leaky waves of the Lamb waves emitted from a detection point on the inner surface of the paper sheet in such a manner that an output direction of the acoustic waves is parallel with an incidence direction of the leaky waves; and
specifying a maximum crest value based on a received signal to judge whether the paper sheet is an unimpaired sheet based on the specified maximum crest value.

10. A paper sheet processor comprising:
a carriage module configured to carry a paper sheet; a bending portion configured to bend the paper sheet carried by the carriage module;
a transmission module configured to transmit acoustic waves to an incidence point on an inner surface of the paper sheet which is bent by the bending portion and is carried, thereby exciting Lamb waves, wherein the transmission module is disposed such that the acoustic waves enters the incident point on the inner surface of the paper sheet at a predetermined angle;
a reception module configured to receive leaky waves of the Lamb waves emitted from a detection point on the inner surface of the paper sheet, wherein the reception module is disposed such that an output direction of the acoustic waves is parallel with an incidence direction of the leaky waves entering the reception module;
a judgment module configured to specify a maximum crest value based on an output from the reception module to judge whether the paper sheet is an unimpaired sheet based on the specified maximum crest value; and
a classification processing module configured to classify the paper sheet based on a judgment result obtained from the judgment module.

* * * * *